(12) United States Patent
Gröhbühl et al.

(10) Patent No.: US 12,251,700 B2
(45) Date of Patent: Mar. 18, 2025

(54) THERMAL CYCLER

(71) Applicant: STRATEC SE, Birkenfeld (DE)

(72) Inventors: Bernd Gröhbühl, Ettlingen (DE); Martin Trump, Pforzheim (DE)

(73) Assignee: STRATEC SE, Birkenfeld (DE)

( * ) Notice: Subject to any disclaimer, the term of this patent is extended or adjusted under 35 U.S.C. 154(b) by 0 days.

(21) Appl. No.: 16/170,319

(22) Filed: Oct. 25, 2018

(65) Prior Publication Data
US 2019/0118183 A1 Apr. 25, 2019

(30) Foreign Application Priority Data

Oct. 25, 2017 (EP) .................................. 17198361
Dec. 22, 2017 (LU) ...................................... 100593

(51) Int. Cl.
*B01L 7/00* (2006.01)
*C12Q 1/686* (2018.01)

(52) U.S. Cl.
CPC ............... *B01L 7/52* (2013.01); *C12Q 1/686* (2013.01); *B01L 2200/026* (2013.01); *B01L 2200/0684* (2013.01); *B01L 2300/0654* (2013.01); *B01L 2300/18* (2013.01); *B01L 2300/1827* (2013.01); *B01L 2300/185* (2013.01); *B01L 2300/1894* (2013.01); *B01L 2400/0622* (2013.01); *B01L 2400/0638* (2013.01); *B01L 2400/0644* (2013.01)

(58) Field of Classification Search
CPC ...... B01L 7/00; B01L 7/54; B01L 2300/0654; B01L 2300/0819; B01L 2300/1822; B01L 2300/1827; B01N 21/0332; G01N 21/6428; G01N 21/6454; G01N 2021/0325; G01N 2021/062
USPC ...................................................... 435/287.2
See application file for complete search history.

(56) References Cited

U.S. PATENT DOCUMENTS

| | | | | |
|---|---|---|---|---|
| 6,382,585 B1 * | 5/2002 | Pubben | ...................... | F16K 7/17 251/243 |
| 6,762,049 B2 * | 7/2004 | Zou | ...................... | B01J 19/0093 435/7.1 |
| 6,940,598 B2 * | 9/2005 | Christel | ...................... | F28F 3/12 356/417 |
| 8,029,733 B2 * | 10/2011 | Chang | ...................... | B01J 19/0093 422/82.07 |
| 9,266,109 B2 * | 2/2016 | Howell | ...................... | B01L 7/52 |
| 9,656,265 B2 | 5/2017 | Adolfsen | | |

(Continued)

FOREIGN PATENT DOCUMENTS

EP 2404676 A1 1/2012
EP 2415855 A1 2/2012
(Continued)

*Primary Examiner* — Michael L Hobbs
*Assistant Examiner* — Lenora A Abel
(74) *Attorney, Agent, or Firm* — William Gray Mitchell

(57) ABSTRACT

A system for thermal cycling, comprising at least one separate vessel holder for taking up a reaction vessel providing a contact surface for the reaction vessel, wherein the vessel holder is surrounded by individual liquid channels for cooling and at least one electrical heater is attached to the at least one separate vessel holder; and a multilayer liquid port for attachment of at least one vessel holder for providing the cooling liquid to the at least one separate vessel holder, and at least one control unit for connecting with the at least one electrical heater.

13 Claims, 16 Drawing Sheets

(56) References Cited

U.S. PATENT DOCUMENTS

| | | |
|---|---|---|
| 2004/0209348 A1 | 10/2004 | Lanz |
| 2006/0065868 A1* | 3/2006 | Strong ................ F16K 31/1221 |
| | | 251/63.5 |
| 2009/0263782 A1* | 10/2009 | Ward ........................ B01L 7/52 |
| | | 435/303.1 |
| 2010/0203595 A1* | 8/2010 | Ward ........................ B01L 7/52 |
| | | 165/181 |
| 2011/0312102 A1 | 12/2011 | Jo |
| 2013/0143272 A1 | 6/2013 | Guo |
| 2014/0073013 A1 | 3/2014 | Gorman |
| 2015/0020532 A1 | 1/2015 | Polaniec |

FOREIGN PATENT DOCUMENTS

| | | |
|---|---|---|
| WO | 9518676 A1 | 7/1995 |
| WO | 2012/063011 | 5/2012 |
| WO | 2012/063011 A2 | 5/2012 |
| WO | 2016074910 A1 | 5/2016 |

\* cited by examiner

Figure 3
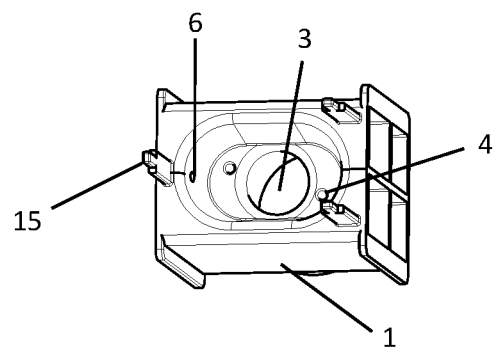
Figure 4A
Figure 4B
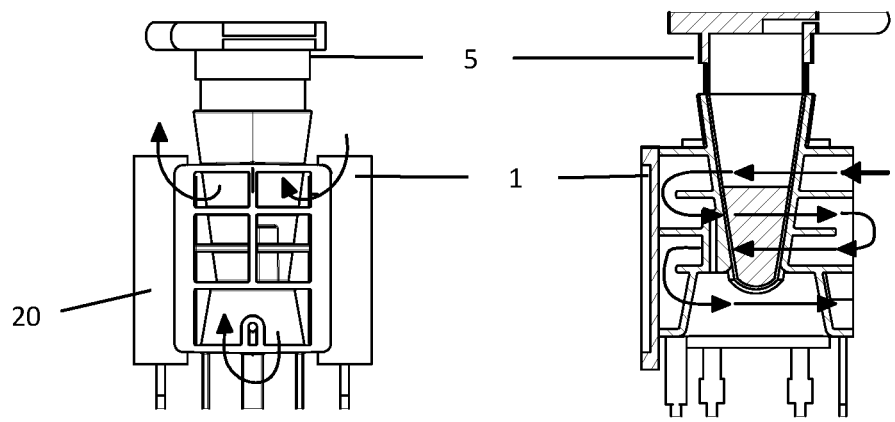

Figure 16A
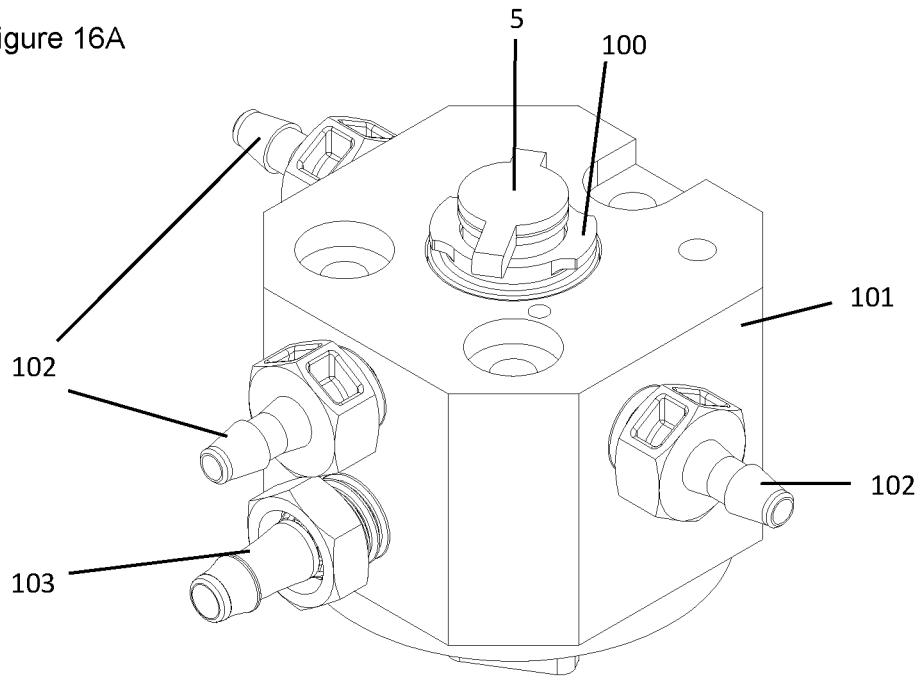
Figure 16B
Figure 16C
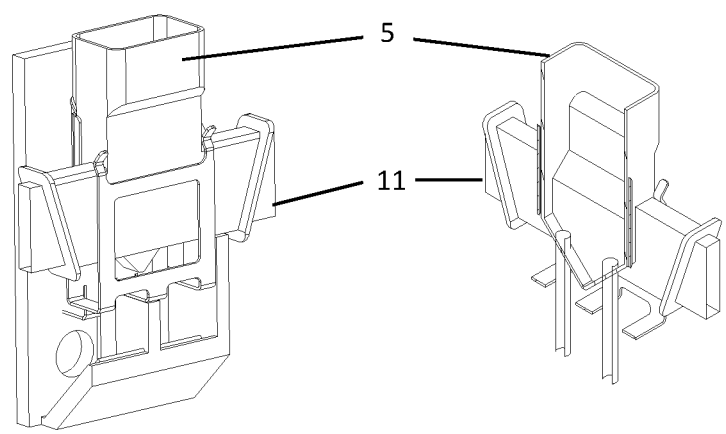

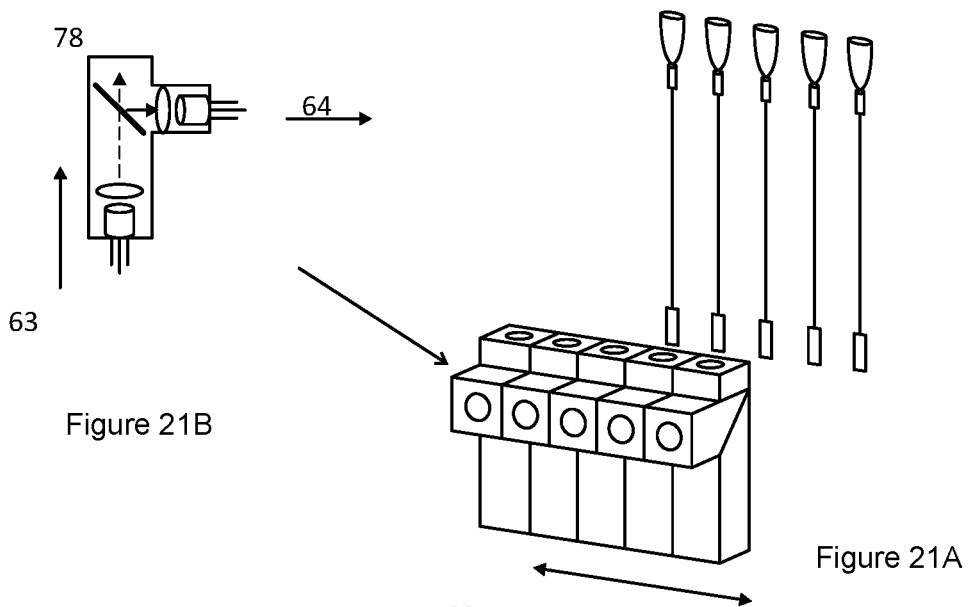
Figure 21B
Figure 21A
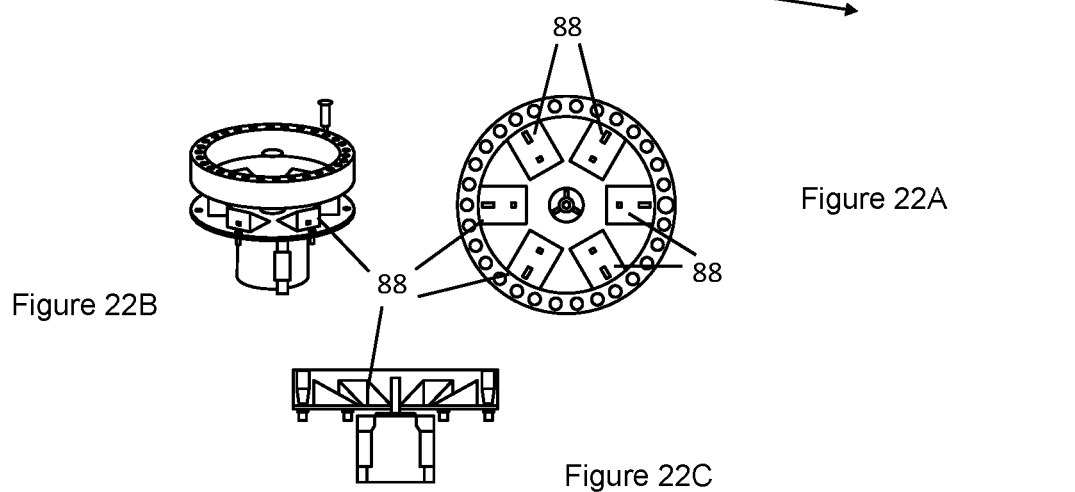
Figure 22A
Figure 22B
Figure 22C
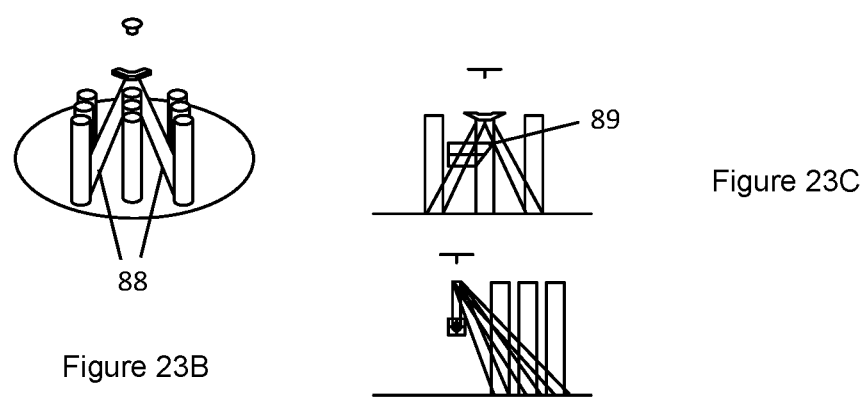
Figure 23C
Figure 23B
Figure 23A

THERMAL CYCLER

CROSS-REFERENCE TO RELATED APPLICATIONS

The present application claims priority to European Patent Application No. EP 17198361.2 filed on Oct. 25, 2017 and Luxemburg Patent Application No. LU 100593 filed on Dec. 22, 2017. The aforementioned applications are hereby incorporated by reference in its entirety.

BACKGROUND OF THE INVENTION

Field of the Invention

The invention relates to a system for thermal cycling enabling PCR (polymerase chain reaction).

Background of the Invention

Automated analyser systems for use in clinical diagnostics and life sciences are produced by a number of companies. For example, the Stratec Biomedical AG, Birkenfeld, Germany, produces a number of devices for specimen handling and detection for use in automated analyser systems and other laboratory instrumentation.

Polymerase chain reaction (PCR) thermal cycling is a method for amplification of specific DNA target sequences. The reaction solutions comprise a reaction buffer, enzymes, primer and nucleotides. This mixture has to undergo repeated changes of temperature to enable amplification of the desired DNA sequence. The repeated change of temperature is referred to as thermal cycling A quantitative analysis during PCR cycling may be achieved by measurement of fluorescence emission.

PCR thermal cyclers are widely used as laboratory stand-alone devices to amplify segments of DNA via the polymerase chain reaction. They usually have one thermal block with holes where single tubes, stripes of tubes, or micro plates holding reaction mixtures can be inserted.

Some of these commonly used heater blocks allow for performing thermal gradients over several tubes at a time. They however cannot treat each tube individually and are not suitable to perform different assays with individual timings and temperature profiles simultaneously.

Thermal cycling (heating/cooling) inside the devices is usually performed by thermos-electrical devices (Peltier elements) and with electrical (resistive) heaters. Only a few other cyclers use different approaches like hot or cool air, previous types of cyclers used several oil or water baths with different temperatures.

Various steps of pre-treatment (e.g. extraction of DNA) and the addition of reaction mixes are typically necessary prior to applying a sample onto a thermal cycler. These steps are often performed manually in a lab environment. Loading and unloading of reaction vessels is usually done manually.

The number and types of fluorescent dyes that can be used and measured in know thermal cycler is limited and refer to the commonly used fluorophores to label DNA probes. It is a disadvantage of known systems that all necessary pre-treatment steps like extraction and purification steps needs to be done externally and manually prior to loading the reaction mix onto a thermal cycler.

A further disadvantage of systems known from the state of the art is that the reaction vessels have to be applied or removed manually. Individual assay processing in different reaction vessels cannot be achieved on known thermal cycler. That prevents a desired variability of assay processing on automated analyser systems.

Standard thermal cycler work usually with quasi standard vials or reaction vessels which still introduce a wide range of mechanical, thermal, and optical performance properties and variations. User are restricted to use only limited numbers of fluorescent dyes that can be used on a standard thermal cycler. Thus, changing to different dyes which might be intended for use is often not possible.

An automatic or robotic handling of standard vial geometries (particularly with individual tubes) is difficult or not feasible within automated analyser systems known from the state of the art.

The ramping speeds related to changes of temperature is limited to the properties of standard vials thus restricting standard heating and cooling technology. As a consequence, the overall processing speed and throughput in a system is limited as well. Scalability like up scaling is only possible by using multiple stand-alone devices.

Commonly used heating and cooling designs generate waste heat close to the core functional area of a thermal cycler making the implementation of heat sinks, fans, air channels etc. necessary resulting in space restrictions at various areas of the thermal cycler.

Published U.S. Patent Application No. US 2004/0209348 A1 discloses a PCR apparatus with a specimen chamber, a heating conduit which communicates with the specimen chamber, a cooling conduit which communicates with the specimen chamber, and a pumping device for pumping a gaseous or liquid medium through the heating conduit and/or the cooling conduit to the specimen chamber. The PCR apparatus further has a heating device, disposed separately from the cooling conduit, which communicates with the heating conduit and heats the medium located in the heating conduit c. The PCR apparatus has further a mixing device, which communicates with the heating conduit and with the cooling conduit, such that a ratio between a volume of the medium flowing per unit of time through the heating conduit and a volume of the medium flowing per unit of time through the cooling conduit to the specimen chamber is adjustable.

In published International Patent Application No. WO 2016074910 A1 a thermocycler and to a method for operating a thermocycler are disclosed. The method for operating the disclosed thermocycler comprises the steps of setting a first temperature in a first temperature region of the sample chamber by means of a first means to denature the nucleic acid strands, setting a second temperature in a second temperature region of the sample chamber by means of a second means to hybridize a primer onto the nucleic acids, adding a sample containing nucleic acid into the first temperature region of the sample chamber of the thermocycler, denaturing the nucleic acids, moving a movable section of the first outer wall in such a way that the section is moved toward the opposite second outer wall and the sample is moved from the first to the second temperature region, hybridizing the primer-nucleic acid molecules onto the nucleic acid strands, moving the movable section of the first outer wall in such a way that the section is moved away from the opposite second outer wall and the sample is moved from the second to the first temperature region, elongating the nucleic acid strands.

Published International Patent Application No. WO 1995018676 A1 describes a method and apparatus for thermal cycling of nucleic acid assays including a blended fluid stream produced from a plurality of constant velocity, constant volume, constant temperature fluid streams wherein to provide a variable temperature, constant velocity, constant volume fluid stream which is introduced into a sample chamber for heating and cooling samples contained therein. By diverting and altering the ratio of the constant temperature fluid streams relative to one another, the blended fluid stream is rapidly variable in temperature, providing for almost instantaneous temperature change within the environment defined by the sample chamber.

In published U.S. Pat. No. 9,656,265 B2 a random access, high-throughput system and a method for preparing a biological sample for polymerase chain reaction (PCR) testing are disclosed. The disclosed system includes a nucleic acid isolation/purification apparatus and a PCR apparatus. The nucleic acid isolation/purification apparatus magnetically captures nucleic acid (NA) solids from the biological sample and then suspends the NA in elution buffer solution. The PCR testing apparatus provides multiple cycles of denaturing, annealing, and elongating thermal cycles. The disclosed PCR testing apparatus includes a multi-vessel thermal cycler array that has a plurality of single-vessel thermal cyclers that is each individually-thermally-controllable so that adjacent single-vessel thermal cyclers can be heated or cooled to different temperatures corresponding to the different thermal cycles of the respective PCR testing process. This document does not disclose separate vessel holder that can be controlled individually as regards temperature, timing and optical measurements.

Published U.S. Patent Application No. US 2011/0312102 A1 discloses a light transmissive temperature control apparatus, a bio-diagnosis apparatus including the transmissive temperature control apparatus, and a method of diagnosing biochemical reaction using the bio-diagnosing apparatus. The light transmissive temperature control apparatus includes at least one tube which is formed of a light transmissive material and configured to contain a sample; and a temperature control unit which accommodates at least a part of the at least one tube which is transparent, guides light to be irradiated onto the at least one tube and controls a temperature of the at least one tube. This document does also not disclose separate vessel holder that can be controlled individually as regards temperature, timing and optical measurements.

Published U.S. Patent Application No. US 2009/263782 A1 discloses an apparatus for biological or chemical reactions, in particular PCR, that includes a heat removal module adapted to receive snugly a reaction vessel in such a manner as to create good thermal conductivity contact between the module and the vessel. The heat removal module of US 2009/263782 A1 is formed of a thermally conductive material having therein a channel adapted for the flow of a coolant liquid. The heat removal module is constructed with an array of receiving stations for the reception of a corresponding array of reaction vessels. This document does also not disclose separate vessel holder that can be controlled individually as regards temperature, timing and optical measurements.

Further thermal cyclers are described in US 2013143272 A1, US 2015020532 A1, EP 2 415 855 A1 and EP 2 404 676 A1.

SUMMARY OF THE INVENTION

It is an object of the present invention to provide a system that can be part of analyser systems that allows for a highly scalable real-time thermal cycling.

The present disclosure provides a device for a system for thermal cycling, comprising at least one separate vessel holder for taking up a reaction vessel providing a contact surface for the reaction vessel, wherein the at least one separate vessel holder is surrounded by individual liquid channels for cooling and at least one individual electrical heater attached to the at least one separate vessel holder for individually adjusting the temperature of the vessel; and a multilayer liquid port for attachment of at least one separate vessel holder for providing the cooling liquid to the at least one separate vessel holder; and at least one control unit for connecting with the at least one electrical heater.

The system may encompass in a further aspect that said at least one separate vessel holder has an optical path access area at its lower side.

It is further envisaged that the optical path access area of the at least one separate vessel holder may have a ventilation channel for its cleaning.

The at least one separate vessel holder may have in a further embodiment an inlet and an outlet for the liquid for cooling at the upper side of the at least one vessel holder.

It is further intended that the at least one separate vessel holder may have an internal fluidic path conveying the liquid for cooling on one side of said at least one separate vessel holder from its upper to its lower side and on its opposite side from its lower to its upper side.

The at least one separate vessel holder may have in a further aspect an acceptance for a maximum of two of the at least one electrical heater at opposite sides.

The at least one control unit can be a printed circuit board (PCB), wherein the PCB can be connected with at least one and a maximum of eight of the at least one separate vessel holder and at least one electrical heating, wherein four of the at least one separate vessel holder and attached at least one electrical heating form a unit.

It is envisaged that the multilayer port may have at least one control valve for each of the at least one separate vessel holder, wherein the at least one control valve can be a 3-port/2-way valve. The at least one control valve may be connected to two membrane valves.

In a further aspect, the membrane valves can be 2-port/2-way valves.

The at least one control valve may be connected to pressurized air for switching over the membranes between the ports.

It is envisaged that the at least one separate vessel holder may have stands for attachment to the PCB.

The at least one electrical heating may have electrical connections for attachment to electrical connections on the PCB for transmission of electricity and controlling the at least one electrical heater.

Four of the at least one separate vessel holder, one multilayer port and one PCB may form a unit.

In a further aspect, the system may additionally comprise an optical detection device. The optical detection device may comprise for each of the at least one separate vessel holder one optical fiber and a dichroic mirror for excitation and emission path.

In a further embodiment, the optical detection device may comprise one optical fiber for excitation and one optical fiber for the emission pathway.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

SUMMARY OF THE FIGURES

The invention will be described on the basis of figures. It will be understood that the embodiments and aspects of the invention described are only examples and do not limit the protective scope of the claims in any way. The invention is defined by the claims and their equivalents. It will be understood that features of one aspect or embodiment of the invention can be combined with a feature of a different aspect or aspects and/or embodiments of the invention, in which:

FIG. 3 shows an optical path access area of the vessel holder.

FIGS. 4A and 4B show an internal fluidic path of a reaction vessel holder.

FIG. 16A shows a perspective view of an embodiment of the present invention with a rotary valve that can open and close access ports for hot and cool liquids, compressed air.

FIG. 16B shows a front view of an embodiment with a vessel of FIG. 6A having inbuilt fluidic channels for a heating and cooling fluid.

FIG. 16C shows a rear view of an embodiment with a vessel of FIG. 6A having inbuilt fluidic channels for a heating and cooling fluid.

FIGS. 21A and 21B show another alternative optical embodiment of the present invention.

FIGS. 22A, 22B and 22C show another alternative optical embodiment of the present invention.

FIGS. 23A, 23B and 23C show another alternative optical embodiment of the present invention.

DETAILED DESCRIPTION OF THE INVENTION

Figure 1:
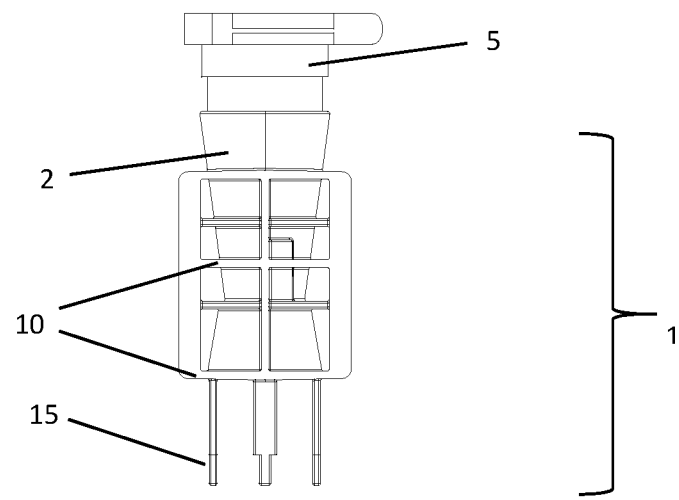
FIG. 1 shows a single reaction vessel holder with a reaction vessel, liquid channels and stands at the bottom.

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

The PCR thermal cycler device according to the present description provides a design that best supports integration in automated analyzer systems. It is designed to be highly scalable in terms of numbers of assay independent compartments (reaction vessel holders) and to process each PCR reaction vessel individually and assay dependent in terms of timing, temperature profile and optical measurement.

In parallel, a specific reaction vessel is designed to be used with this module to improve thermal, optical, and mechanical performance and support robotic handling. The specific reaction vessel design is part of this description. However, some vessels shown in the context of breadboard and prototype development are off the shelf PCR reaction vessels.

The present disclosure relates to the use of a combination of fluidic based cooling and electrical heating to individually temper single reaction vessel holders and the vessels contained therein in a very dense spatial packaging. Document U.S. Pat. No. 9,656,265 B2 does not refer or disclose to the technical solution provided by the present disclosure regarding the combination of fluidic based cooling and electrical heating.

The single reaction vessel holder is designed for low mass and high thermal conductivity to best support fast thermal ramping. It incorporates liquid channels for cooling and provides contact surfaces for electrical heating and conducts to the reaction vessel.

The fluidic approach for cooling allows for high thermal ramping speeds after the denaturation process in a PCR cycle. It also allows for separating the location of where energy for cooling ramping is generated from where it needs to be applied. This provides chances for reduction or elimination of spatial constraints in the vessel holder's arrangement.

An indirect valve based fluidic control is introduced as a means to expose the PCR reaction vessel holder and vessel to cold fluid for thermal ramp-down. Electrical heating in combination with a thermal sensor allows for heating ramp-up and permits to control the temperature during the thermally constant periods of the PCR cycling processes.

The disclosure further relates to specific designs for the electronics architecture, for power supply, temperature control, fluidic paths, as well as for the optical measurement.

All mechanical, fluidics, electronics and optical concepts are designed in a way to best support scalability to make the module fit in various instruments with various throughput. This variability and scalability is another core topic of the invention.

The reaction vessel as the final part of the overall concept is designed to carry an estimated volume of up to 50 μl for the reaction mix. Its design needs to best support thermal contact for heating and cooling, optical contact for fluorescence measurement with optical paths for excitation and emission, protection against evaporation and support for robotic handling Advantages of the invention can be summarized for manufacturing, for automation and for the end user as follows:

FIG. 1 shows a single reaction vessel holder 1 with a reaction vessel 1, liquid channels 10 and stands 15 at the bottom. The vessel holder 1 provides a contact surface 2 for the reaction vessel 5, the cooling liquid, the electrical heaters and thermal sensor(s) and paths for optical measurement and access and stability for automated pick and place of the vessel. The vessel holder 1 shown in FIG. 1 is designed for low mass and high thermal conductivity resulting in fast thermal ramping.

Figure 2:
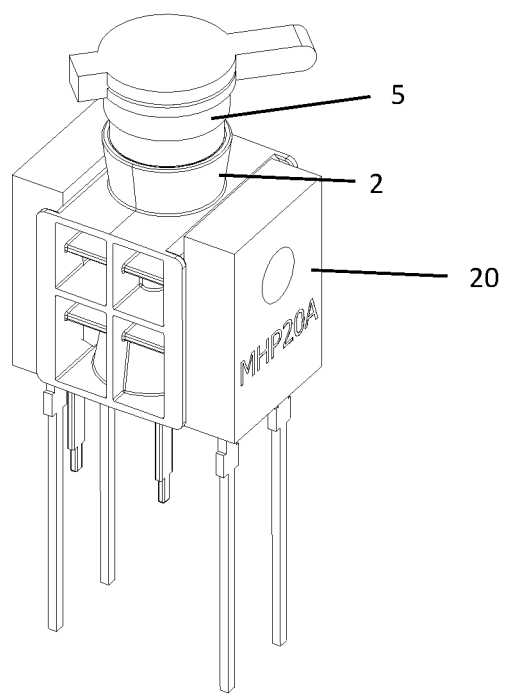
FIG. 2 shows a vessel holder with attached electrical heaters.

FIG. 2 shows the arrangement of FIG. 1 in a 3D view, wherein an electrical heater 20 is attached to the vessel holder 2.

FIG. 3 shows in a bottom view the optical path access area 3 of the vessel holder 1 with indications for thermal sensor placement 4 and a ventilation channel 6 on the left. The ventilation channel 6 serves as a part to keep the top surface of optical fibers that end below reaction vessel 1 clean. Pressurized air is used to blow away dust or particles that might collect on top of the fibers over time. Stands 15 are also indicated.

FIG. 4 shows on the left a side view of a vessel holder 1 with reaction vessel 5 as shown in FIG. 2 with electrical heater 20 and on the right a sectional view rotated by 90 degree to illustrate a key functional element of the reaction vessel holder 1 which is its internal fluidic path. The arrows indicate the flow direction and meandering paths of the liquid. The fluid enters and exits the vessel holder 1 at its top. The fluid stream meanders from the top to the bottom of the holder, then changes sides (left to right) and meanders back up again. The meandering path allows for a reliable exchange of cooling liquid with pressurized air and vice versa. The opposite side of the liquid inlet and outlet ports of the vessel holder is closed.

Figure 5:
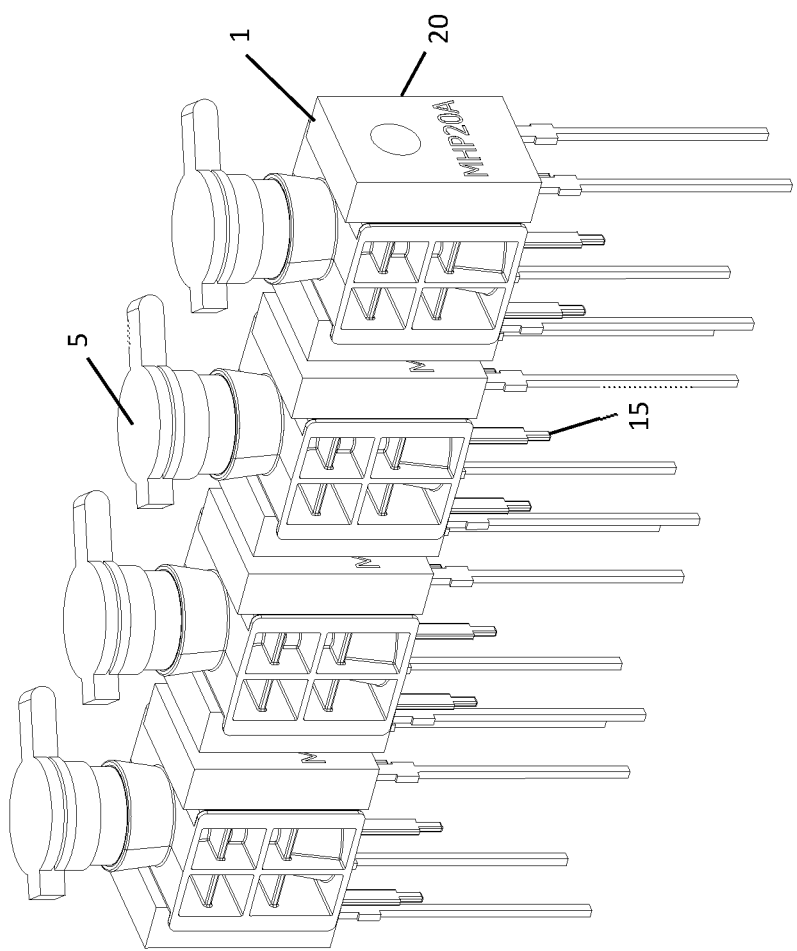
FIG. 5 shows an arrangement of vessel holder.
Figure 6A:
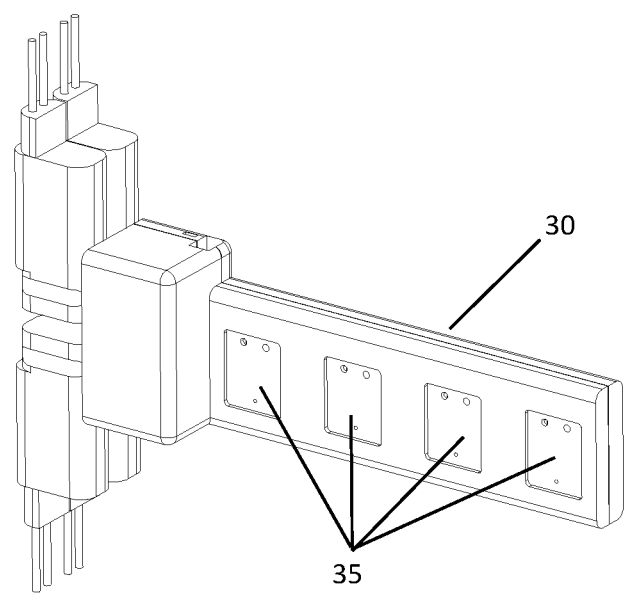
FIGS. 6A and 6B show a multilayer liquid port.
Figure 6B:
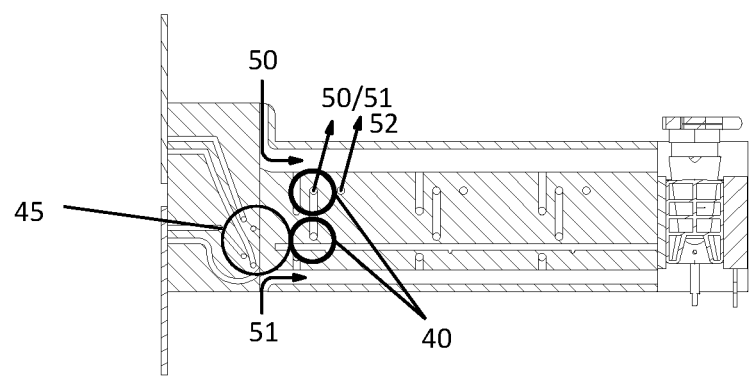

Scalability of the concept concerning the vessel holders 1 with electrical heater 20 can e.g. be achieved by a linear, circular or elliptical array arrangement of vessel holders 1 (FIG. 5). A linear arrangement of four vessel holders 1 with reaction vessel 5 and stands 15 is shown in FIG. 5. This illustrated package of four holders is the smallest unit that is envisaged in one embodiment of the invention. It can be regarded as minimum array for all of the following liquid, optical and electrical scalability considerations and descriptions The liquid connectivity of the four vessel holders is established by a multilayer liquid port 30 as shown in FIG. 6A, which has four sealing contact surfaces 35 for vessel holder with inlet and outlet openings. FIG. 6B shows an embodiment with membrane chambers 40 (circles) on one sealing contact surface. The most left sealing contact surface is hidden by a vessel holder that is attached to it. Beyond the interfaces to the vessel holders (FIG. 6A) it contains the liquid interfaces to the control valves.

One control valve 45 is intended per vessel holder. FIG. 6B shows a more detailed depiction of the membrane valves and membrane chambers 40 inside a liquid port. In total, the liquid port carries four control valves 45 that are visible at the left side of the port. The control valves are 3-port/2-way valves that use pressurized air as a medium to switch over little membrane valves inside the port. The membrane valves are 2-port/2-way valves. Each control valve 45 handles two membrane valves. One of the two membrane valves per vessel holder opens/closes the liquid stream, the other one opens/closes the pressurized air flow through the associated holder. The two membrane valves are alternatingly switched by their corresponding control valve so that either liquid or pressurized air is routed through the holder. The functionality of the membrane valves of the membrane chambers 40 in FIG. 6B are described in more detail below in connection with FIG. 9. Water 50 enters the multilayer liquid port 30 as indicated on the top left and air 51 enters the multilayer liquid port 30 as indicated at the bottom left. An opening for water and air 51/52 is indicated as well as an opening for a reflow 52.

A cooling liquid and pressurized air (at ambient temperature) will be necessary as a supply medium for the system. One 3-port/2-way valve for each vessel holder switches between pressurized air and cooling liquid running through the holder. The default condition is pressurized air.

Figure 7:
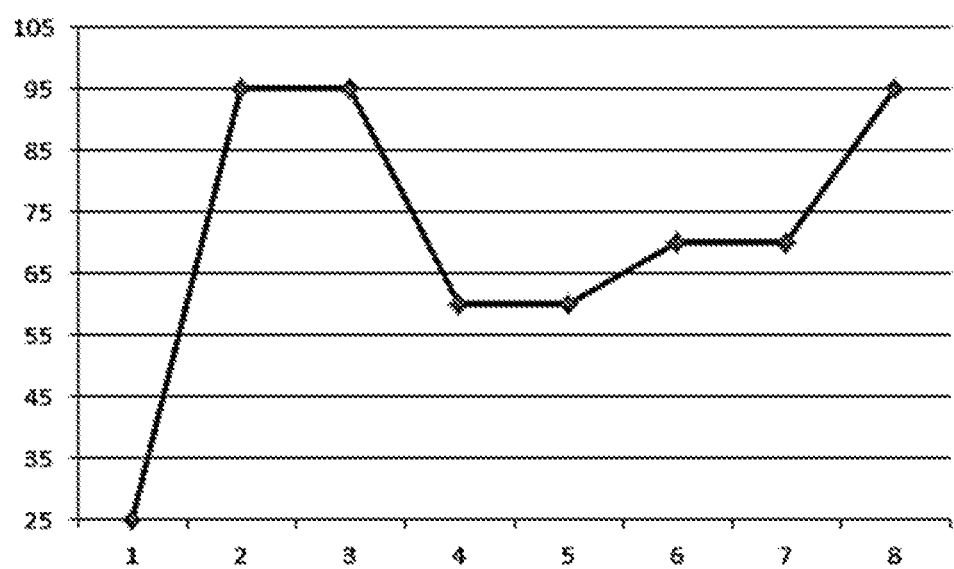
FIG. 7 shows an exemplary a thermal profile of one thermal cycle for a PCR amplification

FIG. 7 shows exemplary a thermal profile of one thermal cycle for a PCR amplification. After an initial heating-up (1-2), a denaturation cycle (2-3) follows and for a temperature drop from e.g. 95° C. to 40-60° C. (3-4), the valve switches to cooling liquid. When afterwards a stable temperature level is required for primer annealing (4-5) the temperature is increased (5-6) for elongation of sequences (6-7) and a ramp for another cycle initiated with denaturation may begin (7-8) or the valve switches back to the default state and the pressurized air pushes liquid residue out of the vessel holder. The electrical heaters are switched on and controlled with the input of the thermal sensor(s).

A collector bottle takes up all drained cooling liquid coming from the vessel holders and cools it down to the required temperature before it is transferred back to the also actively cooled supply reservoir. The pressurized air is ventilated to ambient via a channel in the collector bottle.

The fluidics schematic shows the scalability of the system as each subassembly of vessel holder and switch valve can be added to an existing number of holders (named as 'stackable' in the schematics). As already introduced, a package of four vessel holders with their liquid and electronics supply is the smallest unit for upscaling in this description. Details for that follow below.

Further functionalities like temperature sensing, level sensing, and pressure regulation, further parts like pumps and compressors, liquid and air reservoirs, ventilation and restriction channels are necessary and documented in the schematics to give an overview of the whole fluidic concept.

Figure 8A:
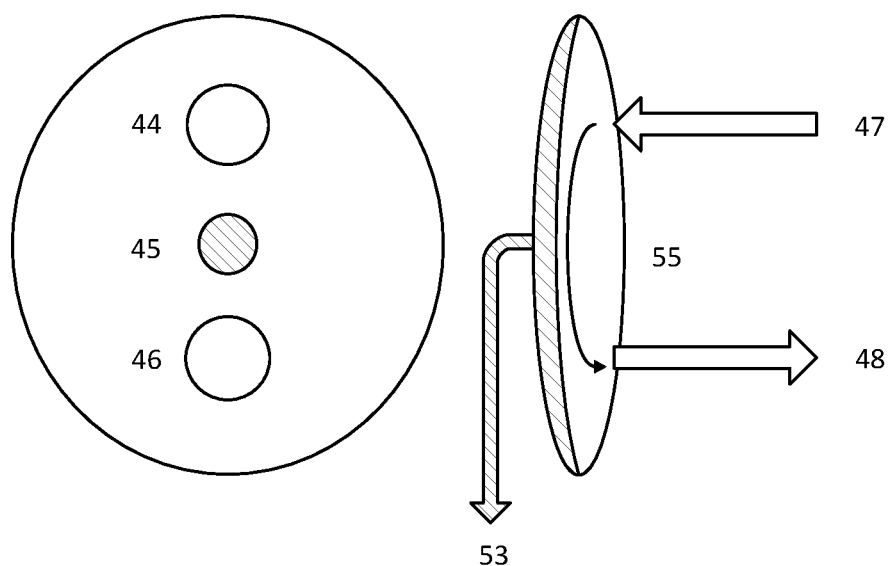
FIGS. 8A and 8B show a functionality of membrane valve.

FIG. 8 shows in detail the functionality of a membrane valve. In FIG. 8A, the control valve 45 ventilates the membrane chamber to ambient 53. As a result, the incoming liquid/air pressure from the supply line 47 can push the membrane open 55 and the liquid or air can stream towards the outlet port 46 and to the vessel holder (not shown).

Figure 8B:
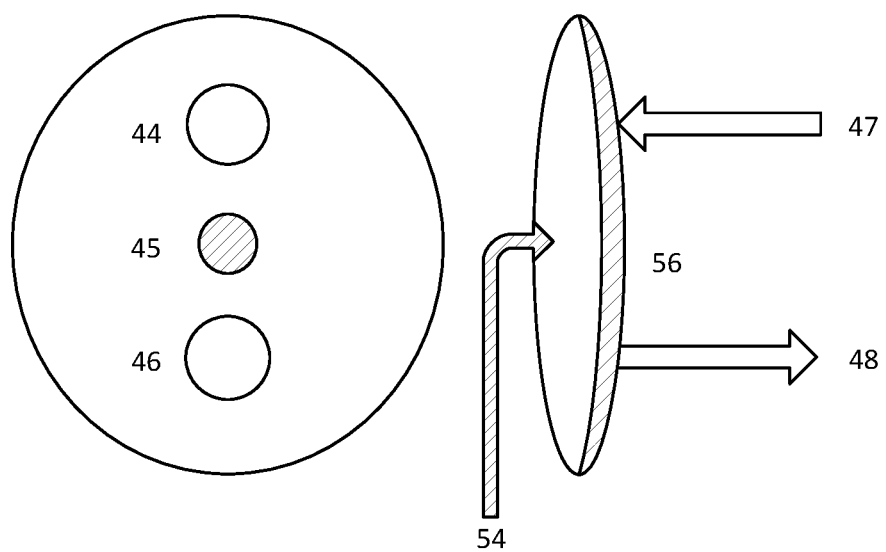

In FIG. 8B, the control valve 45 pressurizes the membrane chamber 54 and so the membrane from the rear. The membrane closes 56 the liquid/air inlet port 44 and the inlet medium is no longer able to stream towards the outlet port 46 and to the vessel holder (not shown).

Figure 9:
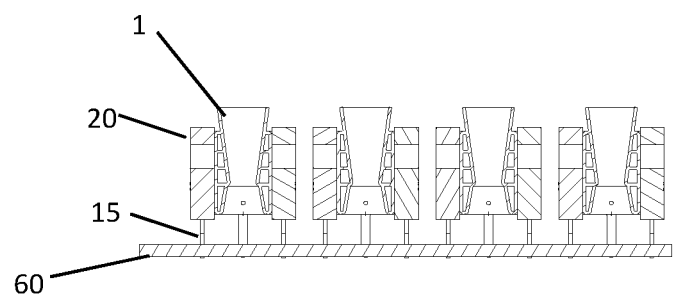
FIG. 9 shows an assembly of control unit printed circuit board assemblies (CU PCBA).

The vessel holders 1 are applied with their stands 15 at the bottom to control unit printed circuit board assemblies (CU PCBA) 60 as can be seen in FIG. 9. It is intended that a CU PCBA 60 is designed to control one or two units each comprising four vessel holders 1. For each additional unit of four vessel holder 1, a further CU PCBA 60 has to be connected to a control unit for the CU PCBAs.

FIG. 9 shows an assembly of CU PCBA 60, vessel holder 1 with reaction vessel 5 and electrical heating element 20. It is to be noted that it is also within the scope of the present invention that the heating element 20 may be printed onto the vessel holder 1 instead of using a separate heating element 20. The CU PCBA 60 contains the power routing, and as the name indicates, carries the vessel holders, the thermal sensors and the electrical heater devices and connectors.

Figure 10A:
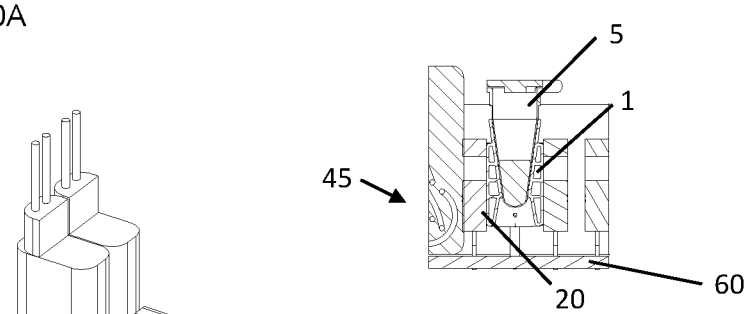
FIGS. 10A and 10B show a smallest scalable unit of four vessel holders on a PCBA with fluidics connection and control valves.
Figure 10B:
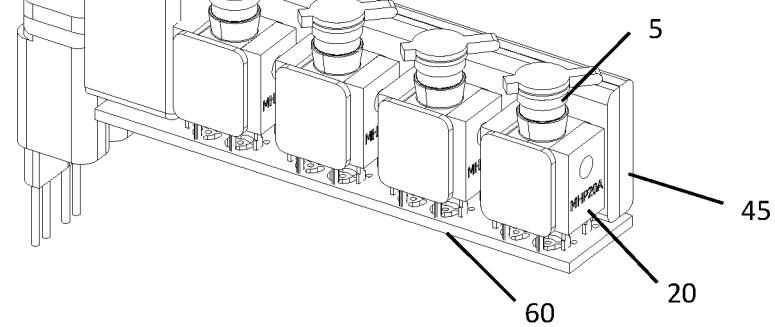

FIG. 10 shows in its top right part a partial crosssectional view of the smallest scalable unit of four vessel holders 1 on a CU PCBA 60 with fluidics connection and control valves 45 and a reaction vessel 5.

For the scalable and potentially high number of PCR reactions running in different vessels at the same time it is necessary to find a way to best support real-time optical measurement of the fluorescence emissions.

As with all PCR reactions in all vessels, starting points, ramping speeds, durations and assay profiles can minimally to widely vary, it is nearly impossible to do a scheduled timing to allow for valid measurements. As for example with 32 vessels and 6 fluorescent dyes this could be 6×32=192 fluorescent excitations/emission readings running in parallel.

For this reason, the designed solution provides a measurement speed that allows for gathering enough measurement points under worst case timing considerations. A following software based interpretation distinguishes between valid and invalid measurement points.

A camera or photo diode is used for emission detection. A camera allows for measuring multiple up to all reaction vessels at one particular fluorescence wavelength at a time. A fast as possible sequence of camera based readings through all fluorescence wavelengths (up to 6) gives the opportunity to measure all vessels in the camera field of view at all different wavelengths within a <4 seconds interval. With the demand that a valid reading can only be performed during the end of an elongation phase of a PCR cycle and under the assumption that the shortest valid reading interval in an elongation phase is considered to be>=4 seconds, at least one valid reading can be performed in every cycle.

Figure 11:
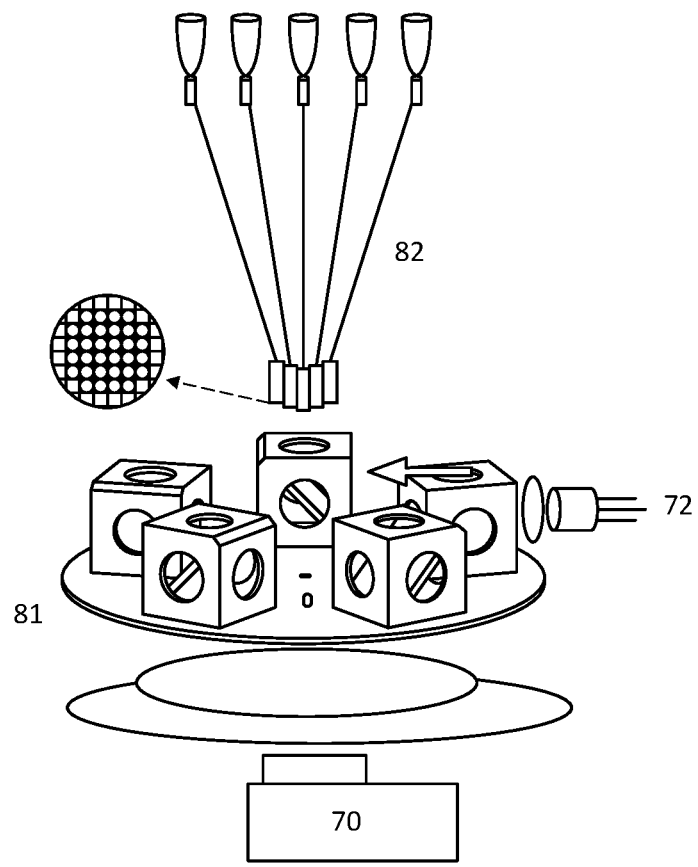
FIG. 11 shows an embodiment with a single fiber.

FIG. 11 shows an embodiment with a single fiber concept, a schematized wireless power supply for individual excitation diodes per channel. The excitation light path is rotating on a carrousel for positioning purposes under the optical fibers 81.

In the design of FIG. 11, one optical fiber 81 per reaction vessel (not shown) is used to:
- maximize the number of reaction vessels monitored in the field of view of camera 70
- allow for a higher number of camera pixels per monitored vessel
- decrease the necessary camera resolution
- eliminate spatial constraints for positioning of camera and vessels
- position the fibers in the center of the fov, etc.

Figure 12:
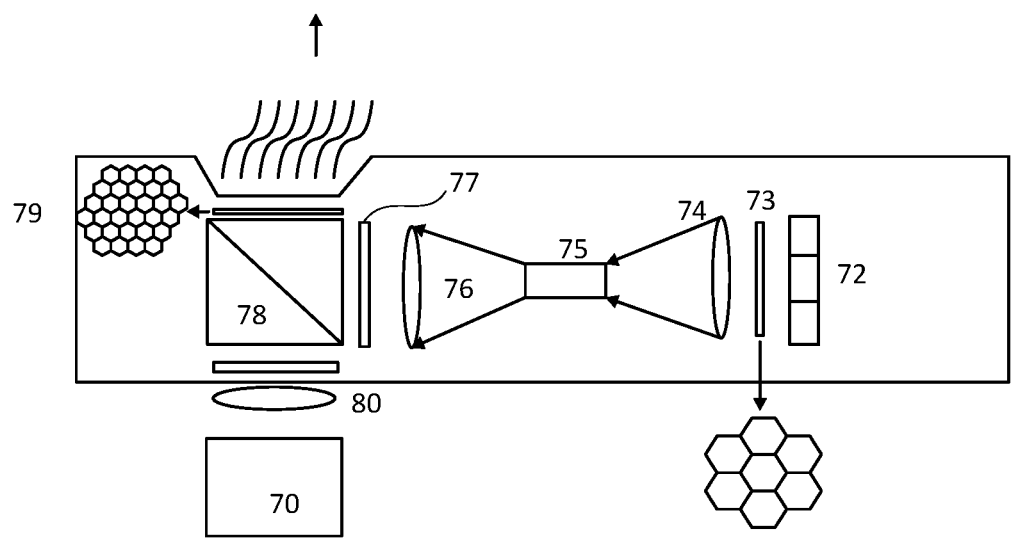
FIG. 12 shows an embodiment with specific dichroic mirror.

Each wavelength specific optical channel is built as a subassembly comparable to the following schematics. A slight emitting laser diode 72 is arranged next to an input lens array 73. The light passes a condenser 74, homogenizer 75, a collimating lens 76 and an excitation filter 77. A fiber lens array 79 is located directly below a vial or is accessing the side of the vial at a tilted angle. Excitation and emission optical paths are separated via a channel specific dichroic mirror 78 as shown in FIG. 12. A camera lens 71 is arranged between camera and emission filter 80

Each of these subassemblies is mounted on a carrousel 81 so it can be positioned in the optical path between fiber lens array 79 and camera 70 by the carrousel drive. The overall number of subassemblies (optical channels) in the module is scalable between one and a maximum number that is limited due to measurement timing restrictions. The described design is heading for a maximum number of six optical channels.

The wireless power supply for the excitation diodes comprises an energy transmitter PCB and a receiver PCB that is attached to the rotating wheel of the carrousel. Wireless power and a communication and control channel are transmitted via inductive coupling.

In case photo diodes are used instead of a camera for this approach, one or more photo diodes need to be mechanically moved to read the emission rates of the bundled fibers in the array one after another. In this case the orientation of the fiber array pattern and diode movement pattern need to match to perform all readings. The number of photo diodes necessary depends on the number of reagent vessels to be read and the reading speeds that can be achieved.

Figure 13:
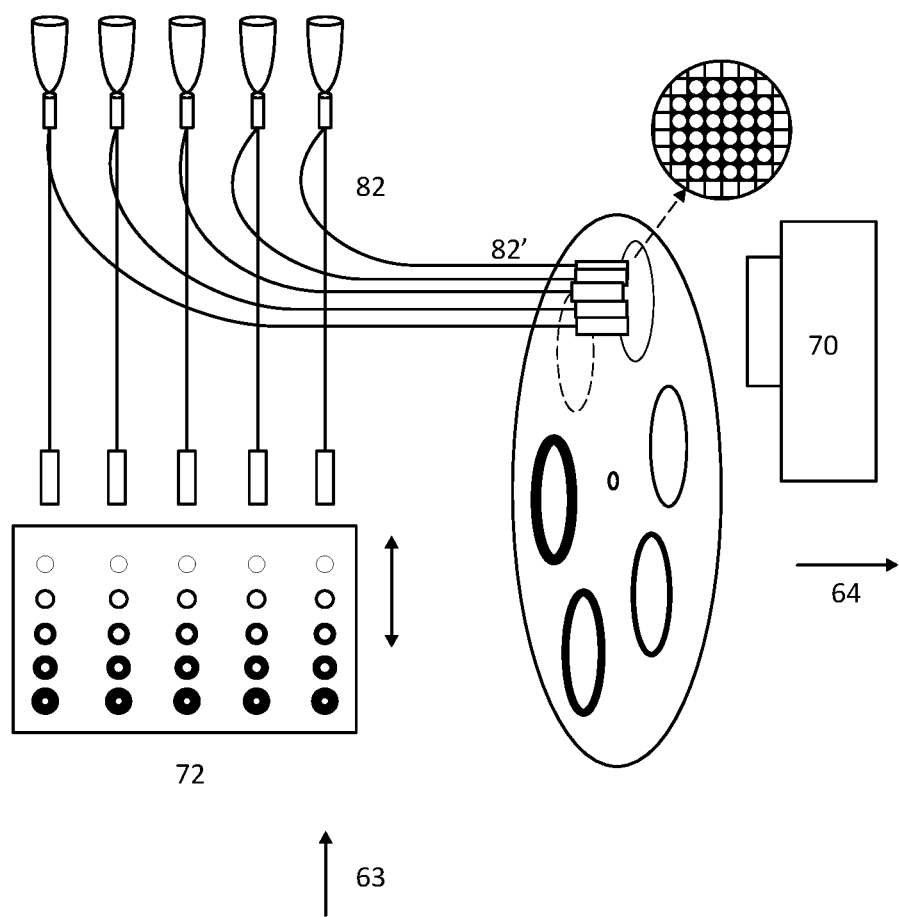
FIG. 13 shows a dual fiber concept.
Figure 14:
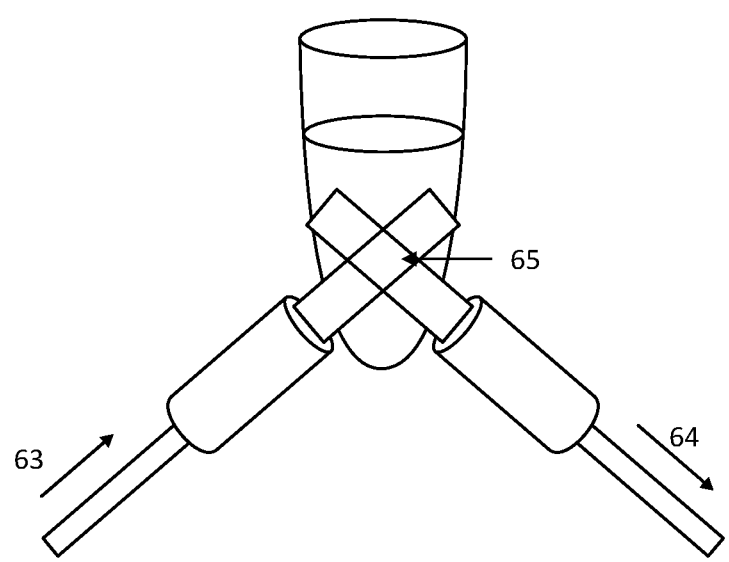
FIG. 14 shows an exemplary depiction of angle between fibers.
Figure 15:
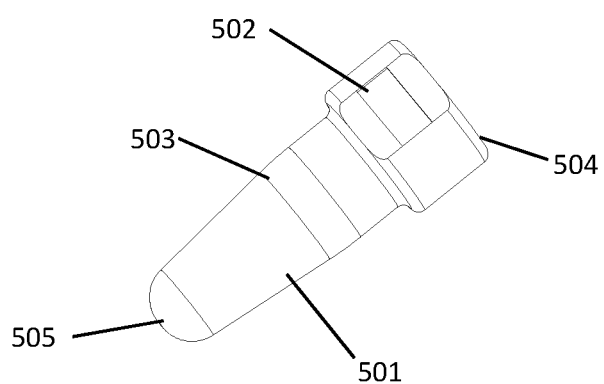
FIG. 15 shows a vessel design.

FIG. 13 shows an embodiment with a dual fiber concept of two optical fibers 82, 82' per reaction vessel (not shown) to achieve the benefits of the single fiber version plus generate additional advantages:
- dichroic mirrors can be avoided.
- the parts that need to be mechanically moved per channel switch can be reduced The optical fibers 82 are located directly below a vial or at a tilted angle below the vial (FIG. 14). Excitation 63 and emission 64 paths use different fibers. At the reagent vessel position excitation and emission fibers can be placed in line or at a defined angle towards each other An installation with a defined angle between the fibers does lead to a controlled reagent vessel volume 65 for excitation and emission as illustrated in FIG. 14. In case photo diodes are used instead of a camera the aspects are comparable to the single fiber solution The vessel design according to the present disclosure and as shown in FIG. 15 has to serve multiple functions:

The core functionality is to safely contain the desired volume of sample and reaction mix, which in the described case is up to 50 µl.

The vessel design further needs to provide the best possible thermal contact between this amount of liquid and surrounding means for heating and cooling by a thermal contact section 501, which can be provided as a thin separation wall with a big contact surface and a good and reliable thermal conductivity.

A transportation interface 502 for the transportation system can be provided for handling the vessel safely to ensure secure application in and take it out of a vessel holder. Additionally, the design may contain a mechanical retention section 503 to maintain a proper seating in the vessel holder and allow for a reliable and reproducible thermal contact between holder and vessel.

The design of the vessel shall prevent evaporation of sample and reaction mix during the thermal cycling by top cover 504. Therefore, it has to be able to contain an additional oil layer on top of sample and reaction mix and has to have a cap/top cover 504 to close the inner vial chamber after all liquid is dispensed into it.

Finally, the vessel design needs to provide optical paths and optical access for the optical measurement during and at the end of thermal cycling. Thin and transparent material at the optical access bottom 505 with a specific shape to best support and optimize the optical paths in this specific area of the reagent vessel is implemented.

In an alternative design, the liquid cooling may be achieved by a direct contact between the fluid and the reaction vessel. FIG. 16A, B show two different embodiments for allowing the fluid to directly heat and cool the reaction vessel. It is also conceivable that only the fluid for cooling or heating will be used adjusting the temperature of the reaction vessel. Mixing cool and hot fluids is another example of tempering the reaction vessel to an intended temperature.

In FIG. 16A a rotary valve is shown that can open and close access ports for hot and cool liquids, compressed air. A rotary valve consists of an inner rotating PCR vial carrier 100 and stationary outer valve housing 101. By rotating the vial carrier 100 contact to a respective liquid port 102 established so that hot, cold or both can flow around the reaction vessel 5. A drainage channel 103 may be permanently open or opened and closed if necessary. The fluid being in contact with the reaction vessel may be mixed with hot or cool fluid in order to increase or lower the temperature. Alternatively, the liquid around the reaction vessel may be flushed out and replaced by hot or cool fluid.

FIGS. 16B and 16C show an embodiment with a vessel 5 having inbuilt fluidic channels for a heating and cooling fluid 11. FIG. 16C shows a look into vessel 5 with cooling fluid supply 11, wherein FIG. 16B shows a view onto vessel 5 mounted onto a sealing surface for the vessel 5. Such an embodiment may be used for quantitative OCR analysis. Various fluids or mixtures of fluids different from water may be used for thermal ramping (heating and cooling) or for maintaining stable temperatures. Various additives may be used for improving specific parameters of the fluids or the process per se.

In the design shown in FIGS. 16B and 16C, one valve indirectly switches between air and cooling fluid supply for the vessel holder. This valve may alternatively operate directly. It is possible that the valve operates with any linear or rotary movement. The vessel holder itself may linearly shift or rotate the vessel or an outer housing for changing the liquid supply and thus obtaining a mixture of liquids.

It is within the scope of such alternatives to use more than one valve for supplying liquids for thermal ramping. More than one reaction vessels can be accommodated in a multi reaction vessel holder to allow for parallel processing of reaction vessels with lower flexibility but less hardware and software effort for obtaining an equivalent throughput in the module.

It is also conceivable to have more than one reaction vessels as part of a one piece multi-vial vessel to achieve the described alternative solutions. A potential liquid flow through the multi-vial vessel could run for instance in parallel around the multi-vials. The described approaches for combining or having inbuilt multi vessels are not limited to any numbers of reactions vessels.

The same applies for the number of vessel holders as shown in FIG. 10. The present invention is not limited to have four vessel holders connected, but also refers to have one of the vessel holder as shown in FIG. 10 to be the smallest unit.

FIGS. 17 to 24 show alternative embodiments for the optical design. The alternatives differ in their implementation of excitation and emission technology as well as in reading out emission.

Figure 17:
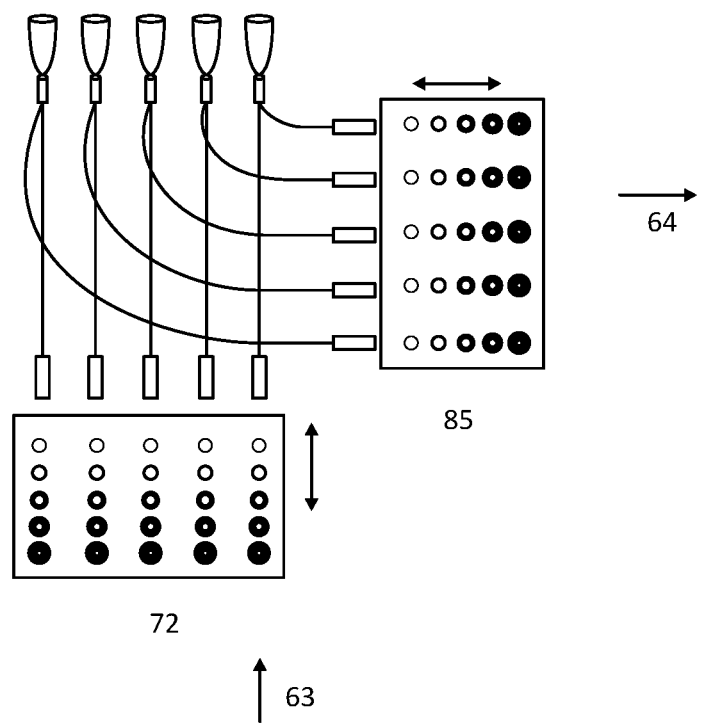
FIG. 17 shows an alternative optical embodiment of the present invention.
Figure 18:
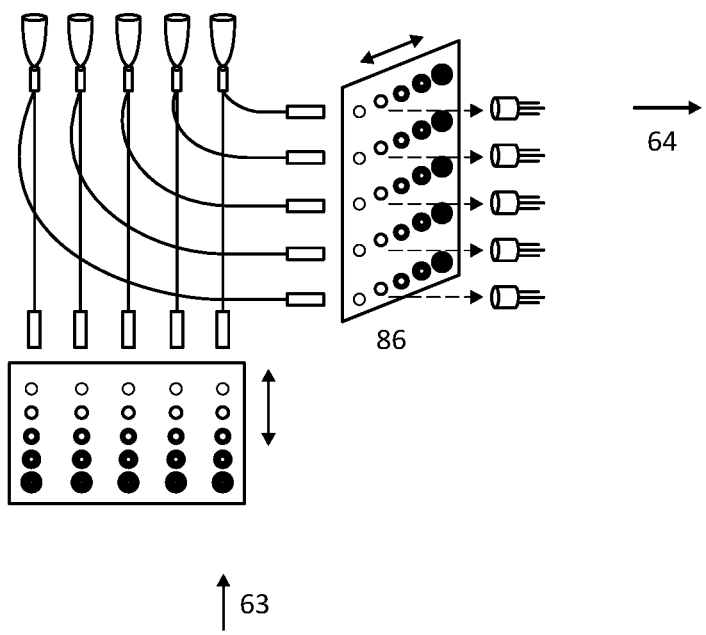
FIG. 18 shows another alternative optical embodiment of the present invention.

FIG. 17 shows an embodiment, with a light emitting/laser diode array 72 being implemented for excitation. Each vessel and every fluorophore would require an individual diode. The number of diodes would be equivalent to the number of vessels multiplied with the number of fluorophores. Similarly, an array of photo diodes 85, one per fluorophore per vessel can be implemented for emission detection. Bifurcated optical fibers can used to couple excitation and emission paths with the vessels FIG. 18 shows an embodiment using broad band photo diodes for emission detection 64. One optical filter per fluorophore per vessel is used to allow read out of the specific wavelength. The filters are arranged in a filter array 86. Bifurcated optical fibers may be used to couple excitation and emission paths with the vessels.

Figure 19:
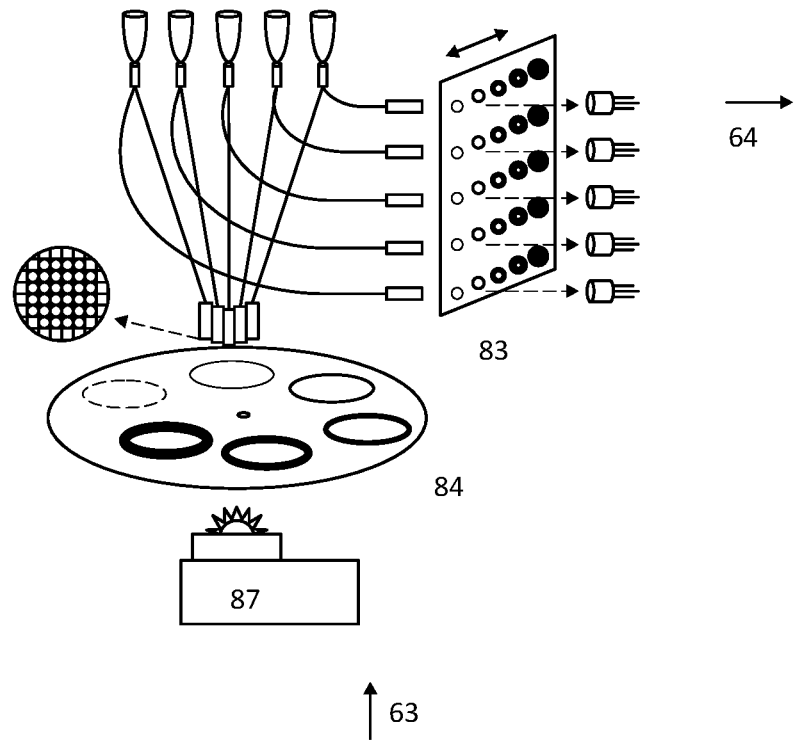
FIG. 19 shows another alternative optical embodiment of the present invention.

FIG. 19 shows an embodiment implementing a broad band light source in combination with a filter wheel 84 for excitation of all channel fluorophores. Bifurcated optical fibers can be used to couple excitation and emission paths with the vessels.

Figure 20:
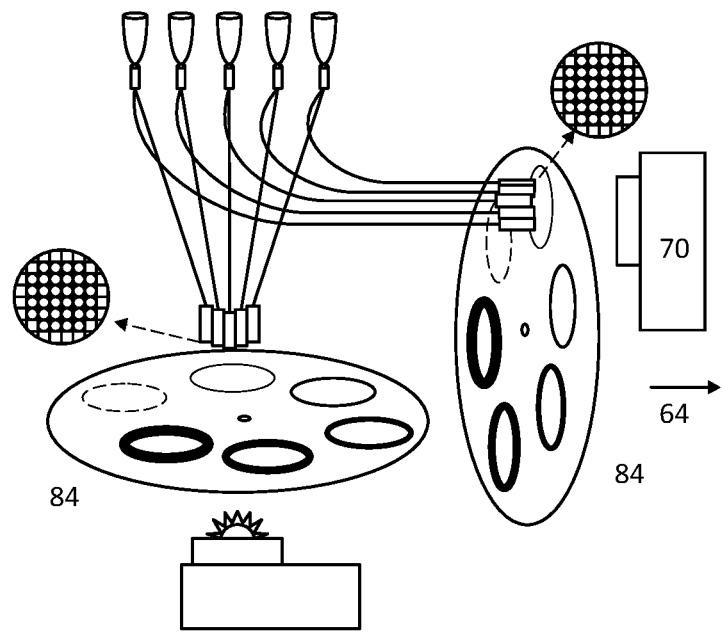
FIG. 20 shows another alternative optical embodiment of the present invention.
Figure 24B:
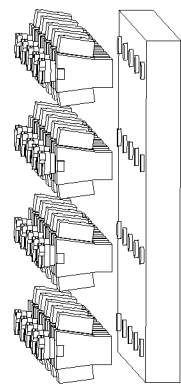
FIGS. 24A, 24B. 24C and 24D show another alternative optical embodiment of the present invention.
Figure 24C:
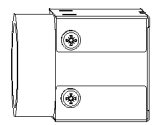
Figure 24A:
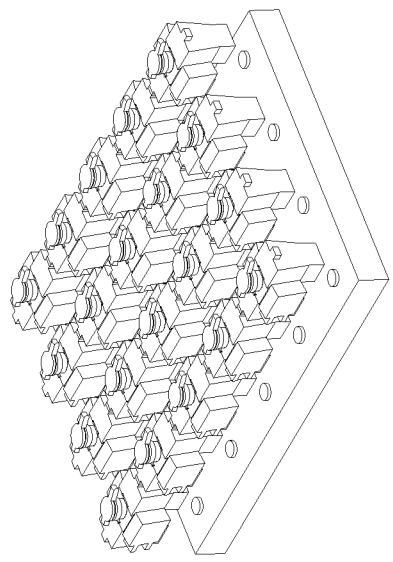
Figure 24D:
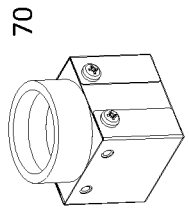

FIG. 20 depicts an embodiment implementing variant filter wheels 84 and a camera into above described designs to perform emission 64 measurement. Any combination of the introduced alternatives for excitation and emission paths is of course also possible.

FIG. 21 shows an embodiment using a dichroic mirror 78 instead of bifurcated fibers to split optical paths for excitation 63 and emission 64. An optical channel subassembly can be built in combination with excitation diodes, filters, lenses and emission detection diodes. Channel subassemblies can be positioned in various orientations (e.g. linear, circular) and coupled with vessels by optical fibers.

FIG. 22 shows an embodiment, wherein optical paths 88 directly end at the reaction vessel and 'look' at it from two different directions, so that a split of the optical paths is not necessary. The reaction vessels can be positioned with respect to the optical channels or vice versa e.g. via a carrousel or linear drive. In this embodiment, a camera may be used to measure more than one or all reaction vessels at a time (as with the described design).

FIG. 23 depicts an embodiment, where optical paths 88 for excitation or emission detection are folded by using moving mirrors 89 to reach various vessel positions. Moving multi-facet mirror arrangements may reach any type of positional arrangement of reaction vessels for excitation and emission measurement.

FIG. 24 shows a further embodiment for emission detection employing a camera with a direct view at a number of reactions/reaction vessels as illustrated on the left side of the figure.

The advantages of the invention can be summarized as follows:
- With a scalable thermal cycler module integrated in an analyzer system all preparation steps prior to the PCR process and the real-time measurement and all loading and unloading of vessels and other consumables, of supplies and waste can be fully automated.
- Widely spread throughput requirements and needs of diverse analyzer systems can perfectly be addressed by the overall scalability of the design.
- The various demands for optical measurement, meaning a wide diversity in number and type of fluorophores and dyes can be addressed similarly.
- Non-standard vessels are implemented and can be used to achieve better and more homogeneous thermal and optical performance and do provide all necessary robotic handling interfaces.
- Individual PCR vessels and vessel compartments allow for individual assay processing in terms of assay protocols, timing, and temperature profiles.
- Ramping speeds can be improved, to allow for shorter PCR cycles, reduced overall processing times and maximized throughput.

Typical spatial restrictions can be avoided as with transport of cooling and heating fluid the generation of energy is separated from the application area.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

REFERENCE NUMERALS 1 reaction vessel holder
2 contact surface reaction vessel
3 optical path access area
4 indications for thermal sensor placement
5 reaction vessel
6 ventilation channel
10 liquid channel
11 cooling fluid supply
15 stands
20 electrical heater
30 multilayer liquid port
35 sealing contact surface vessel holder
40 membrane chamber
44 inlet port
45 control valve
46 outlet port
47 liquid/air from supply
48 liquid/air to holder
50 water
51 air
52 reflow
53 membrane chamber to ambient
54 membrane chamber pressurized
55 open membrane
56 closed membrane
60 control unit printed circuit board (CU PCB)
70 camera
71 camera lens
72 light emitting diode/array
73 input lens array
74 condenser
75 homogenizer
76 collimating lens
77 filter
78 dichronic mirror
79 fiber lens array
80 emission filter
81 caroussel
82, 82' optical fiber
83 optical fiber array
84 filter wheel
85 photo diode array
86 broad band photo diodes
87 broad band light source
88 optical path
100 rotating valve carrier
101 outer valve housing
102 liquid port
103 drainage port
501 thermal contact section
502 transportation interface
503 mechanical retention section
504 top cover
505 optical access bottom

What is claimed is:

1. A system for thermal cycling, comprising:
    at least one separate vessel holder for taking up a single reaction vessel and providing a contact surface for the single reaction vessel, wherein each of the at least one separate single vessel holder comprises:
        an internal individual vertical meandering fluidic path in a descending flow path around the reaction vessel, configured for supplying a cooling liquid or pressurized air on one side of said at least one separate vessel holder from its upper to its lower side and on its opposite side from its lower to its upper side; and
        at least one individual electrical heater attached on opposite sides next to the at least one separate vessel holder for individually adjusting the temperature of the single reaction vessel;
    a multilayer liquid port with at least one sealing contact surface for the at least one separate vessel holder and inlet and outlet openings for the attachment of the at least one separate vessel holder configured for providing the cooling liquid or the pressurized air to the at least one separate vessel holder;
    a 3-port/2-way control valve inside the multilayer liquid port, such control valve connected to (i) a first membrane valve connected to liquid and (ii) a second membrane valve connected to pressurized air, wherein the first and second membrane valves are 2-port/2-way valves and are alternatingly switched on and off by the control valve and the default position of the control valve is pressurized air; and
    at least one control unit for connecting with the at least one electrical heater.

2. The system of claim 1, wherein said at least one separate vessel holder has an optical path access area at its lower side.

3. The system of claim 2, wherein the optical path access area of the at least one separate vessel holder has a ventilation channel for its cleaning.

4. The system of claim 1, wherein the at least one separate vessel separate holder has an inlet and an outlet for the cooling liquid or pressurized air at the upper side of the at least one vessel holder.

5. The system of claim 1, wherein liquid channel of the fluidic path of the at least one separate vessel holder has an acceptance for a maximum of two of the at least one electrical heater at opposite sides.

6. The system of claim 1, wherein the at least one control unit is a printed circuit board (PCB).

7. The system of claim 6, wherein the printed circuit board (PCB) is connected with at least one and a maximum of eight of the at least one separate vessel holder and at least one electrical heater, wherein four of the at least one separate vessel holder attached to at least one electrical heating form a unit.

8. The system of claim 1, wherein the multilayer port has at least one control valve configured for providing the cooling liquid or the pressurized air to each of the at least one separate vessel holder.

9. The system of claim 1, wherein the at least one separate vessel holder has stands for attachment to the printed circuit board (PCB).

10. The system of claim 1, wherein the at least one electrical heating has electrical connections for attachment to electrical connections on the PCB for transmission of electricity and controlling the at least one electrical heater.

11. The system of claim 1, wherein four of the at least one separate vessel holder, one multilayer port and one PCB form a unit.

12. The system of claim 1, further comprising an optical detection device.

13. The system of claim 1, wherein the optical detection device comprises for each of the at least one separate vessel holder one optical fiber and a dichroic mirror for excitation and emission path.

* * * * *